US00PP11648P

United States Patent [19]

Pieters

[11] Patent Number: Plant 11,648

[45] Date of Patent: Nov. 28, 2000

[54] CHRYSANTHEMUM PLANT NAMED 'GEDI WT8'

[76] Inventor: Dirk Pieters, Schierveldestraat 3A, Oosnieuwkerke, 8840 Staden, Belgium

[21] Appl. No.: 09/168,913

[22] Filed: Oct. 8, 1998

[51] Int. Cl.[7] ..... A01H 5/00

[52] U.S. Cl. ..... Plt./294

[58] Field of Search ..... Plt./294, 295

*Primary Examiner*—Howard J. Locker

*Attorney, Agent, or Firm*—Christie, Parker & Hale, LLP

[57] ABSTRACT

A new plant variety of chrysanthemum producing white daisy-type flowers.

1 Drawing Sheet

BACKGROUND OF THE INVENTION

The present invention is directed to a new and distinct variety of chrysanthemum botanically classified as *Dendranthema morifolium*. The varietal denomination of the new chrysanthemum is 'GEDI WT8'.

The new variety is a natural whole plant mutation discovered in a controlled planting of the variety 'Tripoli' (U.S. Plant Pat. No. 10,207) in Staden, Belgium. The new variety has been asexually reproduced by vegetative cuttings in Ventura County, Calif. and the distinguishing characteristics are retained through successive generations of asexual reproduction.

SUMMARY OF THE INVENTION

'GEDI WT8' is a chrysanthemum plant that produces white daisy-type flowers.

COMPARISON WITH PARENTS

'GEDI WT8' differs from its parent in having white ray florets whereas its parent has purple florets.

BRIEF DESCRIPTION OF ILLUSTRATION

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. in the month of July. 'GEDI WT8' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that longevity of individual blooms of 'GEDI WT8' is about 19 days and the response time is about 7 weeks. No growth retardent has been applied in the specimens described. Useful growing conditions include night temperatures of about 62°–65° F. and day temperatures of about 70°–75° F. The new variety is naturally blooming during late September to mid October in Ventura County, Calif.

Plant:

*Habit.*—Nonbrittle, mounding herbaceous perennial.

*Height.*—About 18 cm.

*Number of breaks from pinch.*—About 6 to 7.

*Length of lateral branches.*—About 14 cm.

*Stem color.*—Near 138A.

Foliage:

*Leaf arrangement.*—Alternate.

*Number of leaves per lateral branch.*—About 14 fully expanded leaves.

*Leaf size.*—Length: About 4.8 cm. Width: About 2.9 cm.

*Leaf shape.*—Ovate.

*Attachment.*—Petioled.

*Leaf apex.*—Acute.

*Base.*—Tapered.

*Margin.*—Palmately lobed.

*Aspect.*—Slightly undulate.

*Surface.*—Top: Lightly pubescent. Bottom: Lightly pubescent.

*Midvein.*—Color Upper side: Near 137B. Color Underside: Near 138A.

*Petiole.*—Length: About 1 cm. Color: Near 137B.

*Color.*—Mature leaf: Near 137A. Top: Near 137C. Bottom: Young leaf: Near 137B. Top: Near 138B. Bottom:

Bloom:

*Inflorescence form.*—Cyme.

*Bloom type.*—Daisy.

*Number of blooms per branch.*—About 12.

*Diameter of fully expanded bloom.*—About 4.5 cm.

*Depth of fully expanded bloom.*—About 1.2 cm.

*Diameter of disc.*—About 1.5 cm.

*Sepal number.*—About 30. Color: Near 137B.

*Peduncle.*—Length: 3.5 cm. Surface: Pubescent. Color: Near 138A.

*Flower bud* (*when just showing color*).—Color: Near 27D Diameter: Near 0.7 cm. Height: About 1 cm. Shape: Obovoid

*Ray florets.*—Number per flower: About 30. Texture: Matte. Shape: Oblanceolate. Apex: Obtuse. Base: Tapered. Margin: Entire. Aspect: Slightly recurved. Length: About 2.1 cm. Width: About 0.4 cm.

*Disc florest.*—Number per flower: About 110. Texture: Glossy. Shape: Cylindric. Margin: Entire. Length: About 0.4 cm. Width: About 0.08 cm.

*Fragrance.*—Moderate.

Flower color:

*General flower description.*—White daisy-type with a yellow/orange disc.

*Ray florets, top side.*—Immature: Near 158C. Mature: Near 158D. Fading: Near 158C.

*Ray florets, under side.*—Immature: Near 158C. Mature: Near 158B. Fading: Near 158C.

*Disc florets.*—Immature: Near 154C. Mature: Near 16B. Fading: Near 16A.

*Changes as the flower ages.*—Daisy form becomes very open, abundant. pollen is released.

Reproductive organs:

*Ray florets.*—Pistillate. Stigma shape: 2 branched. Stigma color: Near 2B. Style length: About 0.2 cm. Style color: Near 1D.

*Disc florets.*—Stigma shape: Linear. Stigma color: Near 2B. Style Length: About 0.2 cm. Style color: Near 154D. Stamen number: About 5. Anther length: About 0.2 cm. Pollen color: Near 15B. Pollen quantity: Abundant.

What is claimed is:

1. A new and distinct chrysanthemum plant of the variety substantially as herein shown and described.

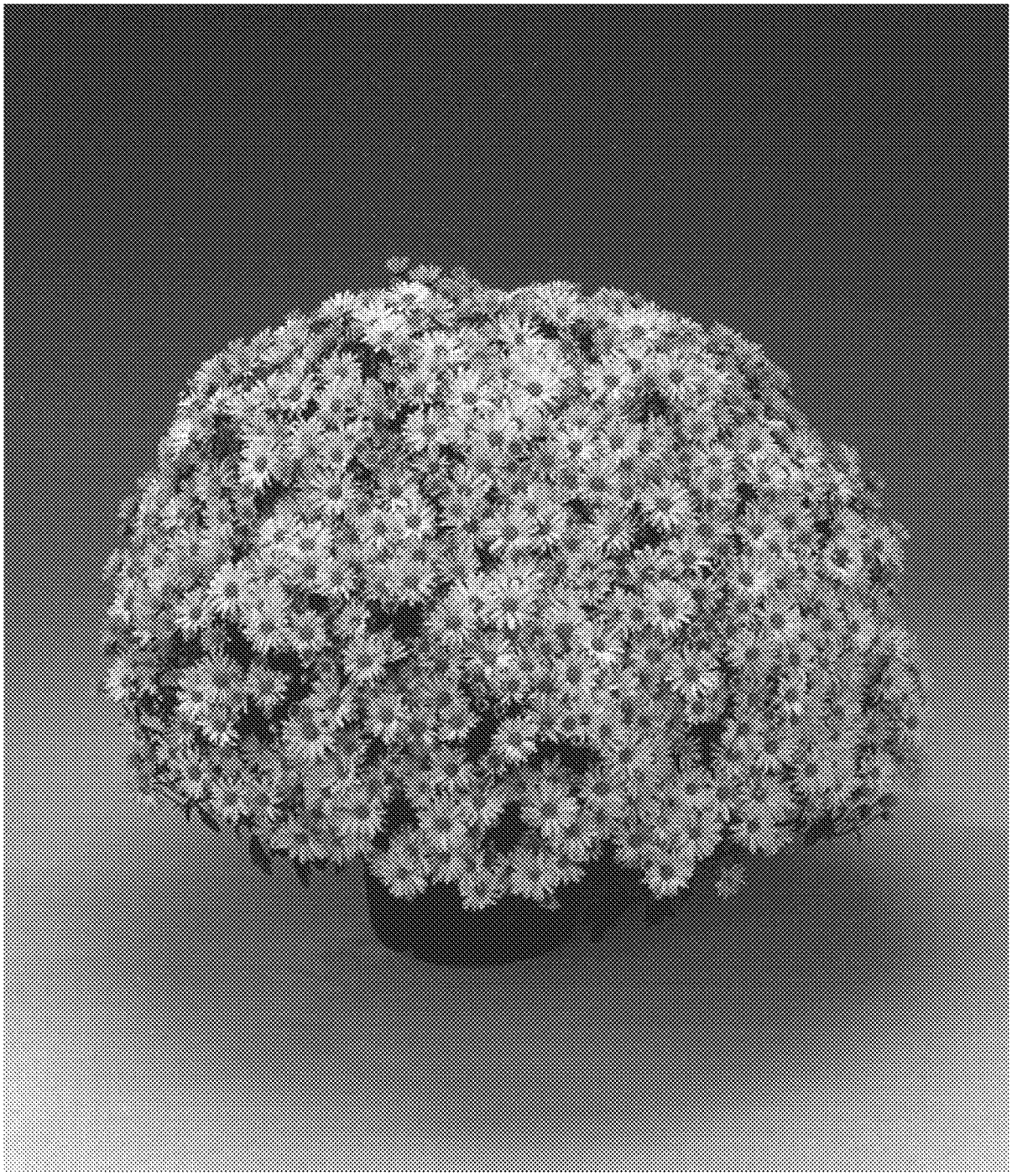

* * * * *